[54] 2-(P-PRENYLPHENYL)PROPIONIC ACID

[75] Inventors: Takehiro Amano, Urawa; Jiro Sawada, Kodaira; Michitada Sasajima, Higashimurayama, all of Japan

[73] Assignee: Taisho Pharmaceutical Co., Ltd., Tokyo, Japan

[21] Appl. No.: 45,090

[22] Filed: Jun. 4, 1979

[30] Foreign Application Priority Data

Jun. 10, 1978 [JP] Japan ................................. 53/70223

[51] Int. Cl.³ ........................................... C07C 69/618
[52] U.S. Cl. .................................... 424/317; 562/495
[58] Field of Search ........................ 562/495; 424/317

[56] References Cited

U.S. PATENT DOCUMENTS 3,385,886  5/1968  Nicholson et al. .................. 562/495

FOREIGN PATENT DOCUMENTS 2316211  1/1978  France .

*Primary Examiner*—Jane S. Myers
*Attorney, Agent, or Firm*—George A. Loud

[57] ABSTRACT

2-(p-prenylphenyl)propionic acid and pharmaceutically acceptable salts thereof are disclosed. They exhibit anti-inflammatory and analgesic activity with low gastrointestinal action.

2 Claims, No Drawings

2-(P-PRENYLPHENYL)PROPIONIC ACID

BACKGROUND OF THE INVENTION

Although many anti-inflammatory and analgesic agents are known today, they generally possess high ulcerogenic action in proportion to their pharmaceutical effect, so the decreasing of said side effect has strongly been needed for these agents.

SUMMARY OF THE INVENTION

The present invention relates to 2-(p-prenylphenyl)-propionic acid and the pharmaceutically acceptable salts thereof.

It has been discovered that the novel compounds of the present invention have excellent anti-inflammatory and analgesic activity and low gastrointestinal action.

Accordingly, it is an object of the present invention to provide these novel compounds valuable as medicines possessing excellent anti-inflammatory and analgesis activity and reduced gastrointestinal action.

DESCRIPTION OF THE PREFERRED EMBODIMENT 2-(p-prenylphenyl)propionic acid, that is, 2-[p-(3-methyl-2-butenyl)phenyl]propionic acid of the present invention may be prepared by hydrolyzing 2-(p-prenylphenyl)-propionitrile.

According to a manner well known in the art, hydrolysis of 2-(p-prenylphenyl)propionitrile may be carried out in a solvent at room temperature or refluxing temperature of the solvent, preferably, in the presence of a base such as a metallic hydroxide (sodium hydroxide, potassium hydroxide and the like). Suitable solvents used in hydrolysis include water, a lower alcohol (methanol, ethanol, isopropyl alcohol and the like), ethylene glycol, tetrahydrofuran, dioxane and a mixture thereof. The reaction time changes by the conditions, and the completion of the reaction may be determined by thin layer chromatography.

The pharmaceutically acceptable salts of 2-(p-prenylphenyl)propionic acid include, but not limited to, a salt of a metal to form a salt in the group of I, II and III of periodical table of element, preferably, sodium, calcium and aluminum salts. These salts may be prepared from the free acid by conventional methods, for example, they are obtained by neutralizing the free acid with a base such as a metallic hydroxide(sodium hydroxide, potassium hydroxide and the like) or a metallic carbonate(sodium hydrogen carbonate, potassium carbonate and the like).

The salts thus obtained may be converted to other salts by utilizing the difference of solubility. For example, by adding calcium chloride or aluminum nitrate to a solution of the sodium salt, the calcium or aluminum salt may be obtained, successively. The isolated and purified salt can also be converted to the free acid being of high purity.

2-(p-prenylphenyl)propionitrile of the starting material in the above method may be prepared by a known manner per se. For example, a metallic(lithium or magnesium) compound derived from ketal of a p-haloacetophenone may be reacted with a prenyl halide(chloride, bromide or iodide) to give 2-methyl-2-(p-prenylphenyl)-1,3-dioxolane. Suitable p-haloacetophenones include p-chloroacetophenone, p-bromoacetophenone and p-iodoacetophenone. 2-methyl-2-(p-prenylphenyl)-1,3-dioxolane may be converted to p-prenylacetophenone in the presence of an acidic catalyst such as hydrochloric acid. p-prenylacetophenone may be reduced with a metallic hydride, and the reduced product may then be treated with a halogenating agent to give the corresponding 1-halo-1-(p-prenylphenyl)ethane. Suitable metallic hydrides used in the reaction include sodium borohydride, lithium aluminum hydride and the like. As the halogenating agents, thionyl chloride, phosphorus tribromide and the like may be used. The halo compound thus obtained may be cyanated with a metallic cyanide such as sodium cyanide, copper cyanide and the like to give 2-(p-prenylphenyl)-propionitrile.

The compounds of the present invention may be used as anti-inflammatory and analgesic agents in mammals. For these purposes, a compound of the present invention may be administered orally in a conventional dosage form such as tablet, capsule or powder prepared according to conventional pharmaceutical practices. A single dose, or preferably 2 to 4 divided daily doses, provided on a basis of about 2–40 mg/Kg/day, is appropriate.

The compounds of the present invention are of extremely low toxicity. The minimum lethal dose in mice or rats is in excess of 1000 mg/Kg of the body weight.

Experiments made on pharmaceutical properties of the compound of the present invention and comparative compounds (ibuprofen and phenylbutazone) are shown as follows: In these experiments, "TA-060" refers to 2-(p-prenylphenyl)propionic acid, and "per os" is abbreviated as "p.o.".

EXPERIMENT 1

Anti-inflammatory activity was evaluated by the method of rat paw edema(Winter et al., J. Pharmacol. Exp. Ther., 141, 369(1963)). Six male Wistar strain rats were used in each group and a volume of the each paw was measured three hours after injection of carrageenin. The results are shown in Table 1.

TABLE 1

|  | dose (mg/Kg, p.o.) | inhibition (%) |
| --- | --- | --- |
| TA-060 | 50 | 35.9 |
|  | 100 | 46.5 |
|  | 200 | 52.1 |
| ibuprofen | 50 | 37.9 |
|  | 100 | 49.5 |
|  | 200 | 52.9 |

EXPERIMENT 2

Male ddY strain mice in groups of ten each were used for the evaluation of analgesic activity by acetic acid writhing test(Koster et al., Federation Proc., 18, 412(1959)). The results are shown in Table 2.

TABLE 2

|  | dose (mg/Kg, p.o.) | inhibition (%) |
| --- | --- | --- |
| TA-060 | 50 | 37.3 |
|  | 100 | 40.0 |
|  | 200 | 62.7 |
| ibuprofen | 50 | 18.6 |
|  | 100 | 37.5 |
|  | 200 | 53.8 |

EXPERIMENT 3

Immediately after the completion of the test described in Experiment 1, the test compound was orally administered to the test rats in a dose twice the dose administered in Experiment 1, and fasting was continued for 18 hours prior to autopsy and evaluation of gastric lesions and liver weight per 100 g of the test rat. The gastric lesions induced were expressed as incidence(number of rats with gastric lesions/number of the rats) and lesion index(sum of areas damaged). The results are shown in Table 3, wherein the values of lesion index and liver weight are mean ± S.E.

TABLE 3

|  | dose (mg/Kg, p.o.) | incidence | lesion index (mm$^2$) | liver weight (g) |
|---|---|---|---|---|
| control | — | 0/12 | 0 | 3.36 ± 0.05 |
| TA-060 | 100 + 200 | 0/12 | 0 | 3.56 ± 0.04 |
| phenylbutazone | 100 + 200 | 12/12 | 4.59 ± 1.35 | 4.23 ± 0.09 |

EXPERIMENT 4

The test compound was suspended in 0.4% CMC solution in an appropriate concentration, and was administered orally once a day at the definite dose (50, 100 or 200 mg/Kg) in each 10 male Wister rats. Additional 10 control rats were received an equivalent volume of the vehicle. Changes of the body weight of the test rats are shown in Table 4. Table 5 shows the hematological findings at day one after 10 days administration. In those tables, the values of body weight, red blood cell and hemoglobin are mean ± S.E.

As shown in Tables 4 and 5, ibuprofen showed a significant decrease in body weight gain, and also red blood cell and hemoglobin counts, on the other hand, TA-060 showed no effect.

TABLE 4

|  | dose (mg/Kg/ day) | body weight (gram) | | |
|---|---|---|---|---|
|  |  | before treatment | after 5 days | after 10 days |
| control | — | 207.4 ± 2.8 | 220.3 ± 2.8 | 233.3 ± 2.7 |
| TA-060 | 50 | 211.5 ± 3.6 | 224.6 ± 3.6 | 239.7 ± 3.2 |
|  | 100 | 210.0 ± 2.5 | 226.4 ± 2.8 | 238.5 ± 2.3 |
|  | 200 | 211.7 ± 3.1 | 221.9 ± 4.6 | 238.3 ± 5.1 |
| ibuprofen | 50 | 208.9 ± 2.7 | 223.6 ± 2.7 | 235.5 ± 3.1 |
|  | 100 | 209.7 ± 2.1 | 222.0 ± 2.2 | 231.9 ± 2.6 |
|  | 200 | 210.8 ± 3.4 | 206.2 ± 2.8* | 216.2 ± 3.9** |

*p <0.01,
**p <0.001

TABLE 5

|  | dose (mg/Kg, p.o.) | red blood cell (× 10$^4$/mm$^3$) | hemoglobin (g/dl) |
|---|---|---|---|
| control | — | 859.9 ± 4.1 | 15.4 ± 0.1 |
| TA-060 | 50 | 864.2 ± 20.2 | 15.2 ± 0.1 |
|  | 100 | 860.8 ± 9.5 | 15.1 ± 0.2 |
|  | 200 | 857.9 ± 15.2 | 15.0 ± 0.2 |
| ibuprofen | 50 | 807.6 ± 23.6* | 15.1 ± 0.2 |
|  | 100 | 718.2 ± 36.3** | 13.9 ± 0.2*** |
|  | 200 | 667.8 ± 27.6** | 11.8 ± 0.5*** |

*p <0.05,
**p <0.01,
***p <0.001

The following examples are illustrative of the present invention.

EXAMPLE 1

(a) To a mixture of 10.2 g of magnesium turnigns, 300 ml of tetrahydrofuran and a few pieces of iodine, was added 3.8 g of 1,2-dibromoethane with stirring under a stream of nitrogen. Additionally, a solution of 93.0 g of 2-(p-bromophenyl)-2-methyl-1,3-dioxolane dissolved in 300 ml of tetrahydrofuran was dropped while keeping the temperature at 50°-55° C. After dropping, the reaction mixture was stirred for 30 minutes, and cooled to room temperature. A solution of 66.0 g of prenyl bromide in 100 ml of tetrahydrofuran was then dropped to the reaction mixture while keeping the reaction temperature at 50°-55° C., which was allowed to stand for overnight at room temperature. A solution of 20 g of ammonium chloride in 50 ml of water was added. The organic layer was decanted, concentrated and dissolved in ethyl ether. The ethereal solution was washed with water, dried, concentrated and distilled to give 69.1 g of 2-methyl-2-(p-prenylphenyl)-1,3-dioxolane, b.p. 106-107 °C/0.10 mmHg.

A solution of 69.0 g of 2-methyl-2-(p-prenylphenyl)-1,3-dioxolane, 8 ml of 6 N hydrochloric acid and 400 ml of acetone was stirred at room temperature for 3 hours. A solution of 5.0 g of sodium hydrogen carbonate and 200 ml of water was added to the solution, which was extracted with ethyl ether after removal of the acetone. The ethereal solution was washed with water, dried, concentrated and distilled to give 54.6 g of p-prenylacetophenone, b.p. 110-112 °C/0.05 mmHg.

To a solution of 20.0 g of p-prenylacetophenone in 200 ml of methanol, 1.5 g of sodium borohydride was added at 20° C. with stirring. After stirring for 4 hours, 300 ml of water was added, the resulting solution was extracted with ethyl ether. The extract was washed with water, dried, concentrated and distilled to give 18.5 g of 1-(p-prenylphenyl)-ethanol, b.p. 107-108 °C/0.30 mmHg.

To a solution of 9.5 g of 1-(p-prenylphenyl)-ethanol, 4.0 ml of pyridine and 60 ml of benzene, a solution of 5.9 g of thionyl chloride in 10 ml of benzene was added dropwise at 0°-5° C. with stirring. After stirring at room temperature for an hour, the reaction mixture was washed with water, aqueous sodium hydrogen carbonate and water successively and dried. Removal of the benzene gave 10.1 g of 1-chloro-1-(p-prenylphenyl)ethane.

A mixture of 21.0 g of 1-chloro-1-(p-prenylphenyl)ethane, 11.3 g of sodium cyanide and 140 ml of dimethylsufoxide was stirred at 60°-65° C. for 7 hours. After cooling, 400 g of ice-water was added and the resulting solution was extracted with n-hexane. The extract was washed with water, concentrated and distilled to give 16.4 g of 2-(p-prenylphenyl)propionitrile, b.p. 108-110 °C/0.28 mmHg.

(b) A mixture of 16.4 g of 2-(p-prenylphenyl)propionitrile, 60 g of sodium hydroxide, 100 ml of water and 120 ml of methanol was stirred at 70°-75° C. for 8 hours. The resulting solution was concentrated and acidified with dilute hydrochloric acid, followed by extraction with ethyl ether and washing with water. The ethereal solution was extracted with 5% aqueous potassium hydroxide solution. The aqueous layer was acidified with dilute hydrochloric acid, and extracted with ether, which was then washed with water, dried over anhydrous magnesium sulfate and decolorized with activated charcoal. The ether was removed to give 15.5 g of 2-(p-prenylphenyl)propionic acid.

$^1$H NMR(CCl$_4$): $\delta$1.42(3H, d, J = 7.2 Hz, $-\overset{|}{C}H-CH_3$), $\delta$1.68(6H, s, $=\overset{|}{C}-CH_3$), $\delta$3.20(2H, d, J = 7.2 Hz, $-CH_2-$), -continued $\delta 3.53 (1H, q, J = 7.2 Hz, -\overset{|}{C}H-)$, $\delta 5.18 (1H, t, J = 7.2 Hz, =\overset{|}{C}-H)$, $\delta 6.80-7.12 (4H, m, Ph-H)$.

EXAMPLE 2

4.8 g of 2-(p-prenylphenyl)propionic acid as prepared in Example 1 was dissolved in 5% aqueous sodium hydroxide solution to adjust to pH 9.0. After evaporation of the water, the resulting solid was recystallized from ethyl acetate to give 4.5 g of sodium 2-(p-prenylphenyl)propionate, colorless prisms, m.p. 65°–66° C.

EXAMPLE 3

4.8 g of 2-(p-prenylphenyl)propionic acid as prepared in Example 1 was dissolved in 5% aqueous sodium hydroxide solution to adjust to pH 9.0. To the solution, 5% aqueous calcium chloride solution was added dropwise until the insoluble calcium salt no longer formed. The aqueous layer was decanted and the residual solid was crystallized from methanol to give 4.2 g of calcium 2-(p-prenylphenyl)propionate, colorless needles, m.p. 64°–65° C.

EXAMPLE 4

3.70 g of calcium 2-(p-prenylphenyl)propionate as prepared in Example 3 was acidified with a solution of 1N hydrochloric acid, and extracted with ethyl ether, which was then washed with water and dried. The ether was removed to give 3.05 g of 2-(p-prenylphenyl)-propionic acid.

Analysis: calculated for $C_{14}H_{18}O_2$: C, 77.03%, H, 8.31%, Found: C, 76.96%, H, 8.33%.

What we claimed is:

1. 2-(p-prenylphenyl)propionic acid and pharmaceutically acceptable salts thereof.

2. A method of treating a mammal for pain or abnormally high fever comprising administering to said mammal an analgesic or anti-inflammatory effective amount of a compound of claim 1.

* * * * *